Feb. 13, 1973 D. L. ARMSTRONG Plant Pat. 3,303
ROSE PLANT
Filed April 15, 1971
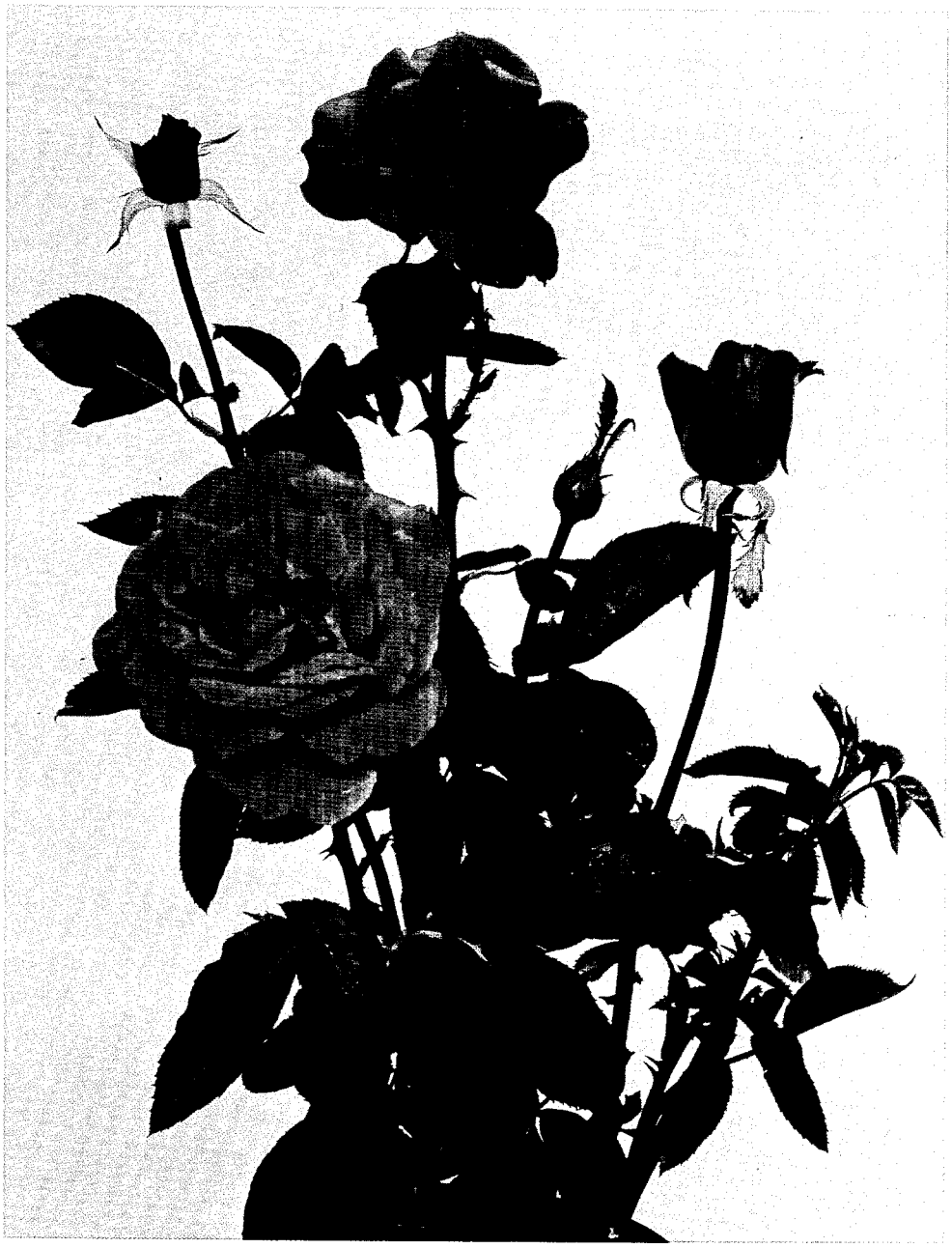

United States Patent Office

Plant Pat. 3,303
Patented Feb. 13, 1973

3,303
ROSE PLANT

David L. Armstrong, Upland, Calif., assignor to
Armstrong Nurseries, Inc., Ontario, Calif.

Filed Apr. 15, 1971, Ser. No. 134,515
Int. Cl. A01h 5/00
U.S. Cl. Plt.—21 1 Claim

ABSTRACT OF THE DISCLOSURE

A new variety of rose plant of the hybrid tea class, particularly vigorous, tall growing and much branched, with long stems and generally smooth peduncles sometimes offset at an angle at the point of attachment to the stem, each stem generally bearing a single flower, but sometimes carrying an irregular cluster of three to four or more. Foliaceous appendages extend beyond the tip of the bud before the calyx breaks to a distance almost equal to the length of the bud. The flowers are dark red in color, with as many as forty-five petals and sixteen petaloids, the bloom being up to six inches in diameter when fully open. Flower petals are medium thick, moderately leathery, and, on exposure to sun, do not show black spots which sun burn often produces on the outer petals of roses which are deep red in color. Flowers on the bush persist for four to five days in the garden and from five to seven days as cut blooms at living-room temperature, in the month of November, in Ontario, Calif.

This invention relates to a new rose of the hybrid tea class. The plant is a seedling of the tall bushy outdoor type, cultivated for cut flowers and for garden decoration. It was propagated by David L. Armstrong in Ontario, Calif., having as its seed parent "John S. Armstrong" (Plant Patent No. 2,056) and, as its pollen parent, "Grand Slam" (Plant Patent No. 2,187). It holds its distinguishing characteristics through succeeding propagations by budding.

The new variety bears its flowers usually singly on strong long stems. Sometimes, however, three or four or more blooms may be carried on one stem in an irregular cluster. The plant blooms abundantly outdoors, and nearly continuously during the growing season. The bloom has a moderate sweetbriar fragrance.

Among the differences between this new variety and its seed parent, John S. Armstrong, the following particulars may be noted:

This new variety is much taller, substantially more upright in its habit, and has stems which are generally longer than the John S. Armstrong plant.

The sepals of this new variety have foliaceous appendages which extend more frequently beyond the tip of the flower bud, and occasionally extend a distance equal to the length of the bud itself, in comparison with the foliaceous appendages of the John S. Armstrong variety which occasionally extend beyond the tip of the bud but for a distance of only one-quarter to one-half of its length.

The flower buds of this new variety are dark red, but they rarely show burn on the outer surfaces, at least at Ontario, Calif., whereas very dark red areas characteristically appear near the tips of the opening bud of John S. Armstrong, which tend to burn on exposure to the sun.

This new cultivar usually produces its flowers singly, and only occasionally three to four or more are carried on one stem. The seed parent produces flowers characteristically in clusters, and only occasionally displays a single flower on a stem. The flowers of this new cultivar are substantially larger than those of John S. Armstrong, ranging from five to six inches in diameter as compared to three and one-half to four inches in the seed parent.

Among the differences between this new variety and its pollen parent, Grand Slam, may be mentioned:

The plants of this new variety are substantially more erect and substantially taller than those of Grand Slam.

The peduncles of this new variety are normally long and heavy, whereas the peduncles of Grand Slam are characteristically of average length and average caliper.

The flower buds of this new variety are normally shorter in relation to their breadth than the buds of Grand Slam, which are slender and long.

The flowers of this new variety have substantially heavier substance than those of the pollen parent, Grand Slam, giving to the new cultivar a lasting quality substantially greater than that of its pollen parent under comparable circumstances.

The flowers of this new variety generally have from 32 to 45 petals and from 11 to 16 petaloids; while in Grand Slam, the petals range from 26 to 30 and the petaloids from 4 to 12.

The color of this new variety is, in popular terms, dark red, while the color of its pollen parent is cherry to rose-red, a substantially lighter color.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

*Bud*

The peduncle is long and heavy, usually erect and stiff, but sometimes bending, and sometimes offset at an angle at the point of attachment to the stem. It is generally smooth, but with a few small stipitate glands. The color is near Moderate Yellow Green, 2.5GY 5/5, overlaid with near Moderate Yellowish Brown, 10YR 4/4, on the side exposed to the sun.

Before the calyx breaks, the bud is medium in size and length, ovoid in form, with slender foliaceous parts occasionally extending beyond the tip of the bud to a distance equal to the bud length.

As the calyx breaks, the color is between Dark Red, 2.5R 3/7, and Dark Red, 5R 3/7.

The inner surface of the sepals carries a fine, woolly tomentum. Margins of alternate sepals are lined with fine, wooly tomentum; margins of others sometimes carry narrow foliaceous parts. The outer surface of the sepals is usually smooth.

As the first petal opens, the bud is average in size, and ovoid to urn-shaped. The color on the outside is between Moderate Red, 2.5R 4/10, and Strong Red, 5R 4/12. The inside surface of the petal is between Dark Red, 2.5R 3/7, and Strong Red, 5R 4/12. The bud opens up well, and is not retarded or prevented from opening by cold, hot, wet, or dry weather.

*Bloom*

The size of the bloom when fully open is large, being from five to six inches across. The petalage is double, with from 32 to 45 petals arranged irregularly, and with 11 to 16 petaloids. The bloom is high centered at first, later becoming open to high centered. At first the petals remain tightly cupped with tips rolled outward. Later, at maturity, they are more loosely flat, and are slightly rolled outward all around the margins.

The petals are of medium thickness, moderately leathery, with inside slightly velvety and the outside slightly shiny to satiny. The shape of the outside petals is from round to very broadly obovate. The intermediate petals are broadly obovate, sometimes slightly scalloped, and sometimes with 1 to 3 notches. The inside petals are obovate, and usually have 1 notch. The colors may be modified by being shaded and/or washed with other colors.

The paragraphs immediately following describe color values observed in a flower newly opened in the month of September. The plant had been grown outdoors in Ontario, Calif.

The outer surface of the outside petal was near Moderate Red, 2.5R 4/10. The inside surface was between Dark Red, 2.5R 3/7, and Strong Red, 5R 4/12.

Both the intermediate petals and the inner petals were near Strong Purplish Red, 10RP 4/12, on the outer surface, and between Moderate Red, 2.5R 4/10, and Strong Red, 5R 4/12, on the inner surface.

The paragraphs immediately following describe color values observed in a bloom which had been open for three days, outdoors, in the month of September, in Ontario, Calif.

The outer surface of the outside petal was between Moderate Red, 2.5R 4/10, and Strong Purplish Red, 10RP 4/12. The inner surface of the outside petal was between Moderate Red, 2.5R 4/10, and Strong Red, 5R 4/12.

The outer surface of the inside petal was between Strong Purplish Red, 7.5RP 4/11, and Strong Purplish Red, 10RP 4/12. The inner surface of the inside petal was the same as the outer surface of the outside petal, namely between Moderate Red, 2.5R 4/10, and Strong Purplish Red, 10RP 4/12.

The general color effect of the newly opened flower is between Moderate Red, 2.5R 4/10, and Strong Red, 5R 4/12. The bloom after being three days open gives a general color effect of between Moderate Red, 2.5R 4/10, and Strong Purplish Red, 10RP 4/12. The petals usually drop off cleanly, except for some petaloids, and are not particularly affected in this respect by cold, hot, wet, or dry weather.

The flower on the bush in the garden persists for from four to five days in the month of November, in the locality named. Cut roses grown outdoors and kept at living-room temperatures will last from five to seven days in the month of November.

*Reproductive organs*

Stamens: There are many stamens, most of them arranged regularly about the pistils, a few of them mixed with petaloids.

Filaments: The filaments are medium-length to long, being from 10 to 15 mm., and their color is near Strong Purplish Red, 7.5RP 5/12. Most are with anthers.

Anthers: The anthers are medium in size, and all open approximately at once. On the upper side the color is near Strong Orange Yellow, 10YR 7/10, on the margins, with the central area being near Strong Orange Yellow, 7.5YR 7/11. On the under side, the color is near Moderate Brown, 5YR 3/3.

Pollen: There is a moderate amount of pollen which is near Strong Orange Yellow, 7.5YR 7/11, in color.

Pistils: There are many pistils, approximately 100.

Styles: The styles are moderately uneven, from average length to long (8 to 14 mm.), of average caliper, and somewhat bunched. The color of the style is near Strong Red, 5R 4/12 just under the stigma, blending to near Light Yellow Green, 7.5GY 9/4, and nearing white at the ovary.

Stigma: The stigma is near Light Orange, 2.5YR 8/6, in color.

Ovaries: Usually, most of the ovaries are enclosed in the calyx. Some protrude from the calyx in older flowers.

Hips: The hips are of average length, globular, with an inconspicuous neck, smooth, with thick fleshy walls. At three-quarters maturity, the color is near Strong Yellow Green, 5GY 6/8.

Sepals: The sepals are permanent. They are medium-length and reflexed. The inside color is near Light Olive, 10Y 5/5, heavily overlaid with fine white tomentum. The outside color is between Strong Yellow Green, 5GY 6/8, and Moderate Yellow Green, 5GY 5/6.

Seeds: Seeds are few to average, usually 2 to 10 in number, and medium in size.

*Foliage*

The compound leaves usually comprise three to five leaflets. They are abundant, medium size to large, somewhat leathery, and semi-glossy. The leaflets are ovate, with apex acute, base round to obtuse, and margin simply serrate.

The mature foliage displays upon its upper surface a near Grayish Olive Green, 5GY 3/2. The under surface is between Moderate Yellow Green, 5GY 5/6, and Moderate Yellow Green, 7.5GY 5/7.

The young foliage displays upon its upper surface a color which is between Dark Red, 5R 3/7, and Moderate Reddish Brown, 7.5R 3/6, but darker in hue. The under surface is near Dark Red, 5R 3/7.

The rachis is average in size, being grooved on the upper side, with some stipitate glands on the edges. The under side carries a few prickles and stipitate glands.

The stipules are medium-length, medium-width, and with medium-length points turning out at an angle of usually less than 45°.

The plant displays an average resistance to mildew, when compared with other varieties now in commerce, when grown at Ontario, California, under comparable conditions.

*Growth*

The plant is upright and spreading in habit, bushy, and much branched. It is vigorous in growth, and has canes of medium caliper.

The main stems are between Moderate Olive Green, 5GY 4/3, and Moderate Yellow Green, 5GY 5/6. They bear several to many large prickles which are medium-length, hooked slightly downward, with long narrow base. Their color is between Brownish Orange, 5YR 5/8, and Strong Brown, 5YR 4/5. There are a few small prickles, and these are the same color as the large prickles. There are no hairs.

The branches are near Moderate Olive Green, 7.5GY 4/4, overlaid with near Moderate Olive Green, 2.5GY 4/3, on the sides exposed to sunlight. There are few to several large prickles which are of medium length , hooked slightly downward, with moderately long base. There are few if any small prickles. Both the large and small prickles are a color near Moderate Reddish Brown, 7.5R 3/6, becoming near Moderate Olive, 5Y 4/3, at the tip. There are no hairs.

New shoots are near Strong Yellow Green, 5GY 6/8, overlaid with near Moderate Reddish Brown, 10R 3/4, on the sides which are exposed to sunlight. There are several large prickles which are medium-length, hooked slightly downward, with moderately long, narrow base. There are few if any small prickles. Both the large and small prickles are a color near Dark Red, 5R 3/7, becoming nearly Light Olive, 7.5Y 5/5, at the tip. There are no hairs.

I claim:

1. A new variety of rose plant of the hybrid tea class, substantially as herein shown and described, said plant further being characterized by a plurality of combinations of features, including: Its vigorous and tall habit of growth, many branched and long stemmed; the relatively smooth peduncles, normally erect but sometimes angled or slightly curved; foliaceous appendages which often extend beyond the tip of the bud for a distance almost equal to its length; its tendency to bear its flowers one to a stem rather than in clusters; the size of the flowers ranging up to six inches in diameter and having double petalage with numerous petaloids, and upwards of 100 stamens; said plant being further characterized not only by its deep red coloration, but also by the freedom of the bud from the development of spots frequently produced by sun burn on deep red rosebuds of other varieties; and also characterized by the longevity of the bloom in a southern California climate, being from 4 to 5 days in the garden, and 5 to 7 days if cut and kept at living-room temperature.

No references cited.

ROBERT E. BAGWILL, Primary Examiner